United States Patent
Zheng (10) Patent No.: US 11,596,726 B2
(45) Date of Patent: Mar. 7, 2023

(54) ULTRASOUND DEVICES FOR REMOVING CLOTS FROM CATHETERS AND RELATED METHODS

(71) Applicant: C.R. Bard, Inc., Tempe, AZ (US)

(72) Inventor: Peng Zheng, Chandler, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 432 days.

(21) Appl. No.: 15/845,187

(22) Filed: Dec. 18, 2017

(65) Prior Publication Data

US 2018/0168668 A1   Jun. 21, 2018

Related U.S. Application Data

(60) Provisional application No. 62/435,723, filed on Dec. 17, 2016.

(51) Int. Cl.
*A61B 17/22* (2006.01)
*A61M 1/36* (2006.01)
*A61M 25/00* (2006.01)

(52) U.S. Cl.
CPC .......... *A61M 1/3659* (2014.02); *A61M 25/00* (2013.01); *A61B 2017/22014* (2013.01); *A61M 2025/0019* (2013.01)

(58) Field of Classification Search
CPC .......... A61M 2025/0019; A61M 5/001; A61M 25/003; A61M 25/0067; A61M 1/0058;
(Continued)

(56) References Cited

U.S. PATENT DOCUMENTS

| 3,296,620 A | 1/1967 | Rodda |
| 3,433,226 A | 3/1969 | Boyd |

(Continued)

FOREIGN PATENT DOCUMENTS

| AU | 2007240154 A1 | 1/2008 |
| DE | 2256127 A1 | 5/1974 |

(Continued)

OTHER PUBLICATIONS

Calhoun et al., "Electron-Beam Systems for Medical Device Sterilization", downloaded from web on Oct. 8, 2002 <http://www.devicelink.com/mpb/archive/97/07/002.html> 7 pages total.

(Continued)

*Primary Examiner* — Bhisma Mehta
*Assistant Examiner* — William R Frehe
(74) *Attorney, Agent, or Firm* — Dinsmore & Shohl LLP (57) ABSTRACT

An apparatus is for use in a vascular space in a body. A catheter has a lumen adapted for communicating fluid between a distal end for insertion in the vascular space and a proximal end. A transducer is adapted for removably connecting to the catheter for contacting the fluid and transmitting energy through the fluid in the lumen for dissolving an obstruction therein. A suction is provided for removing any debris from the obstruction in the lumen of the catheter. The wave guide may be tubular, and may have a length corresponding to the length of the lumen. A catheter or an implantable port including an embedded ultrasonic transducer is also provided.

17 Claims, 8 Drawing Sheets

(58) Field of Classification Search
CPC .... A61M 1/0062; A61M 1/0064; A61M 1/30; A61M 1/301; A61B 2017/320072; A61B 2218/007; A61B 17/320068
See application file for complete search history.

(56) References Cited

U.S. PATENT DOCUMENTS

| | | |
|---|---|---|
| 3,443,226 A | 5/1969 | Knight |
| 3,565,062 A | 2/1971 | Kurls |
| 3,585,082 A | 6/1971 | Siller |
| 3,612,038 A | 10/1971 | Halligan |
| 3,631,848 A | 1/1972 | Muller |
| 3,679,378 A | 7/1972 | Van Impe et al. |
| 3,719,737 A | 3/1973 | Vaillancourt et al. |
| 3,739,460 A | 6/1973 | Addis et al. |
| 3,754,746 A | 8/1973 | Thiele |
| 3,823,717 A | 7/1974 | Pohlman et al. |
| 3,835,690 A | 9/1974 | Leonhardt et al. |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance et al. |
| 4,417,578 A | 11/1983 | Banko |
| 4,425,115 A | 1/1984 | Wuchinich |
| 4,453,935 A | 6/1984 | Newton |
| 4,486,680 A | 12/1984 | Bonnet et al. |
| 4,495,232 A | 1/1985 | Bauser et al. |
| 4,505,767 A | 3/1985 | Quin |
| 4,535,759 A | 8/1985 | Polk et al. |
| 4,545,767 A | 10/1985 | Suzuki et al. |
| 4,565,589 A | 1/1986 | Harrison |
| 4,565,787 A | 1/1986 | Bossle et al. |
| 4,572,184 A * | 2/1986 | Stohl ............... G10K 11/24 606/128 |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,781,186 A | 11/1988 | Simpson et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMicheal et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 4,979,952 A | 12/1990 | Kubota et al. |
| 5,000,185 A | 3/1991 | Yock |
| 5,015,227 A | 5/1991 | Broadwin et al. |
| 5,026,384 A | 6/1991 | Farr et al. |
| 5,030,201 A | 7/1991 | Palestrant |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai et al. |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,131,393 A | 7/1992 | Ishiguro et al. |
| 5,156,143 A | 10/1992 | Bocquet et al. |
| 5,163,421 A | 11/1992 | Bernstein et al. |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,217,565 A | 6/1993 | Kou et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,236,414 A | 8/1993 | Takasu |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,279,546 A | 1/1994 | Mische et al. |
| 5,287,858 A | 2/1994 | Hammerslag et al. |
| 5,290,229 A | 3/1994 | Paskar |
| 5,304,115 A * | 4/1994 | Pflueger ............ A61B 17/22012 606/169 |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'Neill et al. |
| 5,325,860 A | 7/1994 | Seward et al. |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,469 A * | 9/1994 | Ikeda ............... A61B 17/320068 606/171 |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita et al. |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,391,144 A | 2/1995 | Sakurai et al. |
| 5,397,293 A | 3/1995 | Alliger et al. |
| 5,397,301 A | 3/1995 | Pflueger et al. |
| 5,403,324 A | 4/1995 | Ciervo et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,449,370 A | 9/1995 | Vaitekunas |
| 5,451,209 A | 9/1995 | Ainsworth et al. |
| 5,462,529 A | 10/1995 | Simpson et al. |
| 5,465,733 A | 11/1995 | Hinohara et al. |
| 5,474,530 A | 12/1995 | Passafaro et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,498,236 A | 3/1996 | Dubrul et al. |
| 5,507,738 A | 4/1996 | Ciervo |
| 5,516,043 A | 5/1996 | Manna et al. |
| 5,527,273 A | 6/1996 | Manna et al. |

(56) References Cited

U.S. PATENT DOCUMENTS

| | | | |
|---|---|---|---|
| 5,538,512 A | 7/1996 | Zenzon et al. | |
| 5,540,656 A | 7/1996 | Pflueger et al. | |
| 5,542,917 A | 8/1996 | Nita et al. | |
| 5,597,497 A | 1/1997 | Dean et al. | |
| 5,597,882 A | 1/1997 | Schiller et al. | |
| 5,607,421 A | 3/1997 | Jeevanandam et al. | |
| 5,611,807 A | 3/1997 | O'Boyle | |
| 5,618,266 A | 4/1997 | Liprie | |
| 5,626,593 A | 5/1997 | Imran | |
| 5,627,365 A | 5/1997 | Chiba et al. | |
| 5,630,795 A * | 5/1997 | Kuramoto | A61B 1/00137 604/35 |
| 5,649,935 A | 7/1997 | Kremer et al. | |
| 5,658,282 A | 8/1997 | Daw et al. | |
| 5,665,062 A | 9/1997 | Houser | |
| 5,685,841 A | 11/1997 | Mackool | |
| 5,695,460 A | 12/1997 | Siegel et al. | |
| 5,695,507 A | 12/1997 | Auth et al. | |
| 5,715,825 A | 2/1998 | Crowley | |
| 5,720,724 A | 2/1998 | Ressemann et al. | |
| 5,725,494 A * | 3/1998 | Brisken | A61B 17/2202 606/169 |
| 5,728,062 A | 3/1998 | Brisken | |
| 5,738,100 A | 4/1998 | Yagami et al. | |
| 5,797,876 A | 8/1998 | Spears et al. | |
| 5,816,923 A | 10/1998 | Milo et al. | |
| 5,827,203 A | 10/1998 | Nita | |
| 5,827,971 A | 10/1998 | Hale et al. | |
| 5,830,127 A * | 11/1998 | DeCastro | A61B 1/122 600/153 |
| 5,830,222 A | 11/1998 | Makower | |
| 5,846,218 A | 12/1998 | Brisken et al. | |
| 5,873,835 A | 2/1999 | Hastings et al. | |
| 5,876,385 A | 3/1999 | Ikari et al. | |
| 5,893,838 A | 4/1999 | Daoud et al. | |
| 5,895,397 A | 4/1999 | Jang et al. | |
| 5,902,287 A | 5/1999 | Martin | |
| 5,904,667 A | 5/1999 | Falwell | |
| 5,916,192 A | 6/1999 | Nita et al. | |
| 5,916,912 A | 6/1999 | Ames et al. | |
| 5,935,142 A | 8/1999 | Hood | |
| 5,935,144 A | 8/1999 | Estabrook | |
| 5,937,301 A | 8/1999 | Gardner et al. | |
| 5,944,737 A | 8/1999 | Tsonton et al. | |
| 5,957,882 A | 9/1999 | Nita et al. | |
| 5,957,899 A | 9/1999 | Spears et al. | |
| 5,964,223 A | 10/1999 | Baran | |
| 5,967,984 A | 10/1999 | Chu et al. | |
| 5,971,949 A | 10/1999 | Levin et al. | |
| 5,976,119 A | 11/1999 | Spears et al. | |
| 5,989,208 A | 11/1999 | Nita | |
| 5,989,275 A | 11/1999 | Estabrook et al. | |
| 5,997,497 A | 12/1999 | Nita et al. | |
| 6,004,280 A | 12/1999 | Buck et al. | |
| 6,004,335 A | 12/1999 | Vaitekunas et al. | |
| 6,007,499 A | 12/1999 | Martin et al. | |
| 6,007,514 A | 12/1999 | Nita | |
| 6,022,309 A | 2/2000 | Celliers et al. | |
| 6,024,764 A | 2/2000 | Schroeppel | |
| 6,029,671 A | 2/2000 | Stevens et al. | |
| 6,030,357 A | 2/2000 | Daoud et al. | |
| 6,036,689 A | 3/2000 | Tu et al. | |
| 6,047,431 A * | 4/2000 | Canonica | B08B 9/045 15/104.095 |
| 6,051,010 A | 4/2000 | DiMatteo et al. | |
| 6,066,135 A | 5/2000 | Honda | |
| 6,113,558 A | 9/2000 | Rosenschein et al. | |
| 6,120,515 A | 9/2000 | Rogers et al. | |
| 6,123,698 A | 9/2000 | Spears et al. | |
| 6,142,971 A | 11/2000 | Daoud et al. | |
| 6,149,596 A | 11/2000 | Bancroft | |
| 6,159,176 A | 12/2000 | Broadwin et al. | |
| 6,159,187 A | 12/2000 | Park et al. | |
| 6,165,127 A | 12/2000 | Crowley | |
| 6,165,188 A | 12/2000 | Saadat et al. | |
| 6,179,809 B1 | 1/2001 | Khairkhahan et al. | |
| 6,180,059 B1 | 1/2001 | Divino, Jr. et al. | |
| 6,190,353 B1 | 2/2001 | Makower et al. | |
| 6,206,842 B1 | 3/2001 | Tu et al. | |
| 6,210,356 B1 | 4/2001 | Anderson et al. | |
| 6,217,543 B1 | 4/2001 | Anis et al. | |
| 6,217,565 B1 | 4/2001 | Cohen | |
| 6,217,588 B1 | 4/2001 | Jerger et al. | |
| 6,221,015 B1 | 4/2001 | Yock | |
| 6,231,546 B1 | 5/2001 | Milo et al. | |
| 6,231,587 B1 | 5/2001 | Makower | |
| 6,235,007 B1 | 5/2001 | Divino, Jr. et al. | |
| 6,241,692 B1 | 6/2001 | Tu et al. | |
| 6,241,703 B1 | 6/2001 | Levin et al. | |
| 6,241,744 B1 | 6/2001 | Imran et al. | |
| 6,248,087 B1 | 6/2001 | Spears et al. | |
| 6,277,084 B1 | 8/2001 | Abele et al. | |
| 6,283,983 B1 | 9/2001 | Makower et al. | |
| 6,287,271 B1 | 9/2001 | Dubrul et al. | |
| 6,287,285 B1 | 9/2001 | Michal et al. | |
| 6,287,317 B1 | 9/2001 | Makower et al. | |
| 6,296,620 B1 | 10/2001 | Gesswein et al. | |
| 6,298,620 B1 | 10/2001 | Hatzinikolas | |
| 6,302,875 B1 | 10/2001 | Makower et al. | |
| 6,309,358 B1 | 10/2001 | Okubo | |
| 6,315,741 B1 | 11/2001 | Martin et al. | |
| 6,315,754 B1 | 11/2001 | Daoud et al. | |
| 6,331,171 B1 | 12/2001 | Cohen | |
| 6,346,192 B2 | 2/2002 | Buhr et al. | |
| 6,379,378 B1 | 4/2002 | Werneth et al. | |
| 6,387,109 B1 | 5/2002 | Davison et al. | |
| 6,387,324 B1 | 5/2002 | Patterson et al. | |
| 6,394,956 B1 | 5/2002 | Chandrasekaran et al. | |
| 6,398,736 B1 | 6/2002 | Seward | |
| 6,409,673 B2 | 6/2002 | Yock | |
| 6,416,533 B1 | 7/2002 | Gobin et al. | |
| 6,423,026 B1 | 7/2002 | Gesswein et al. | |
| 6,427,118 B1 | 7/2002 | Suzuki | |
| 6,433,464 B2 | 8/2002 | Jones | |
| 6,434,418 B1 | 8/2002 | Neal et al. | |
| 6,450,975 B1 | 9/2002 | Brennan et al. | |
| 6,454,737 B1 | 9/2002 | Nita et al. | |
| 6,454,757 B1 | 9/2002 | Nita et al. | |
| 6,454,997 B1 | 9/2002 | Divino, Jr. et al. | |
| 6,484,052 B1 | 11/2002 | Visuri et al. | |
| 6,491,707 B2 | 12/2002 | Makower et al. | |
| 6,494,891 B1 | 12/2002 | Cornish et al. | |
| 6,494,894 B2 | 12/2002 | Mirarchi | |
| 6,500,141 B1 | 12/2002 | Irion et al. | |
| 6,508,781 B1 | 1/2003 | Brennan et al. | |
| 6,508,784 B1 | 1/2003 | Shu | |
| 6,511,458 B2 | 1/2003 | Milo et al. | |
| 6,514,249 B1 | 2/2003 | Maguire et al. | |
| 6,524,251 B2 | 2/2003 | Rabiner et al. | |
| 6,533,766 B1 | 3/2003 | Patterson et al. | |
| 6,544,215 B1 | 4/2003 | Bencini et al. | |
| 6,547,754 B1 | 4/2003 | Evans et al. | |
| 6,547,788 B1 | 4/2003 | Maguire et al. | |
| 6,551,337 B1 | 4/2003 | Rabiner et al. | |
| 6,554,846 B2 | 4/2003 | Hamilton et al. | |
| 6,555,059 B1 | 4/2003 | Myrick et al. | |
| 6,558,502 B2 | 5/2003 | Divino, Jr. et al. | |
| 6,562,031 B2 | 5/2003 | Chandrasekaran et al. | |
| 6,573,470 B1 | 6/2003 | Brown et al. | |
| 6,576,807 B1 | 6/2003 | Brunelot et al. | |
| 6,582,387 B2 | 6/2003 | Derek et al. | |
| 6,589,253 B1 | 7/2003 | Cornish et al. | |
| 6,595,989 B1 | 7/2003 | Schaer | |
| 6,596,235 B2 | 7/2003 | Divino, Jr. et al. | |
| 6,602,467 B1 | 8/2003 | Divino, Jr. et al. | |
| 6,602,468 B2 | 8/2003 | Patterson et al. | |
| 6,605,217 B2 | 8/2003 | Buhr et al. | |
| 6,607,698 B1 | 8/2003 | Spears et al. | |
| 6,610,077 B1 | 8/2003 | Hancock et al. | |
| 6,613,280 B2 | 9/2003 | Myrick et al. | |
| 6,615,062 B2 | 9/2003 | Ryan et al. | |
| 6,616,617 B1 | 9/2003 | Ferrera et al. | |
| 6,622,542 B2 | 9/2003 | Derek et al. | |
| 6,623,448 B2 | 9/2003 | Slater | |

(56) References Cited

U.S. PATENT DOCUMENTS

| | | |
|---|---|---|
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner et al. |
| 6,676,900 B1 | 1/2004 | Divino, Jr. et al. |
| 6,681,783 B2 * | 1/2004 | Kawazoe .............. A61B 1/122 134/167 C |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,814,727 B2 | 11/2004 | Mansouri-Ruiz |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 * | 2/2009 | Rabiner ................ A61N 7/022 600/459 |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,628,763 B2 | 12/2009 | Noriega et al. |
| 7,648,478 B2 | 1/2010 | Soltani et al. |
| 7,758,510 B2 | 7/2010 | Nita et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,942,809 B2 | 5/2011 | Leban |
| 7,955,293 B2 | 6/2011 | Nita et al. |
| 7,993,308 B2 | 8/2011 | Rule et al. |
| 8,038,693 B2 | 10/2011 | Allen |
| 8,043,251 B2 | 10/2011 | Nita et al. |
| 8,052,607 B2 | 11/2011 | Byrd |
| 8,083,727 B2 | 12/2011 | Kugler et al. |
| 8,133,236 B2 | 3/2012 | Nita |
| 8,152,753 B2 | 4/2012 | Nita et al. |
| 8,172,758 B2 | 5/2012 | Harhen |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'connor |
| 8,308,677 B2 | 11/2012 | Nita et al. |
| 8,343,134 B2 | 1/2013 | Kost et al. |
| 8,403,856 B2 * | 3/2013 | Corl ........................ A61B 8/12 606/14 |
| 8,414,543 B2 | 4/2013 | Mcguckin, Jr. et al. |
| 8,496,669 B2 | 7/2013 | Nita et al. |
| 8,506,519 B2 | 8/2013 | Nita |
| 8,613,700 B2 | 12/2013 | Ueno et al. |
| 8,613,751 B2 | 12/2013 | Nita et al. |
| 8,617,096 B2 | 12/2013 | Nita et al. |
| 8,632,560 B2 | 1/2014 | Pal et al. |
| 8,641,630 B2 | 2/2014 | Nita et al. |
| 8,647,293 B2 | 2/2014 | Nita |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,702,595 B2 | 4/2014 | Ueki |
| 8,708,892 B2 | 4/2014 | Sugiyama et al. |
| 8,708,994 B2 | 4/2014 | Pettis et al. |
| 8,725,228 B2 | 5/2014 | Koblish et al. |
| 8,764,700 B2 | 7/2014 | Zhang et al. |
| 8,768,433 B2 | 7/2014 | Jenkins et al. |
| 8,790,291 B2 | 7/2014 | Nita et al. |
| 8,974,446 B2 | 3/2015 | Nguyen et al. |
| 8,978,478 B2 | 3/2015 | Ishioka |
| 9,101,387 B2 | 8/2015 | Plowe et al. |
| 9,107,590 B2 | 8/2015 | Hansmann et al. |
| 9,237,837 B2 | 1/2016 | Omoto et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,433,433 B2 | 9/2016 | Nita et al. |
| 9,603,615 B2 | 3/2017 | Sarge |
| 9,770,250 B2 | 9/2017 | Nita et al. |
| 9,955,994 B2 | 5/2018 | Nita |
| 10,004,520 B2 | 6/2018 | Nita et al. |
| 2002/0022858 A1 | 2/2002 | Demond et al. |
| 2002/0049409 A1 | 4/2002 | Noda et al. |
| 2002/0077550 A1 | 6/2002 | Rabiner et al. |
| 2002/0188276 A1 | 12/2002 | Evans et al. |
| 2002/0189357 A1 | 12/2002 | Lai et al. |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0019349 A1 | 1/2004 | Fuimaono et al. |
| 2004/0024393 A1 | 2/2004 | Nita et al. |
| 2004/0054367 A1 | 3/2004 | Teodoro, Jr. et al. |
| 2004/0082884 A1 * | 4/2004 | Pal ........................ A61B 17/16 601/2 |
| 2004/0164030 A1 | 8/2004 | Lowe et al. |
| 2004/0167511 A1 | 8/2004 | Buehlmann et al. |
| 2004/0193033 A1 | 9/2004 | Badehi et al. |
| 2005/0033311 A1 | 2/2005 | Guldfeldt et al. |
| 2005/0149110 A1 | 7/2005 | Wholey et al. |
| 2005/0165388 A1 | 7/2005 | Bhola |
| 2005/0171527 A1 | 8/2005 | Bhola |
| 2005/0215946 A1 * | 9/2005 | Hansmann ............ A61B 8/0808 606/41 |
| 2005/0228286 A1 | 10/2005 | Messerly et al. |
| 2006/0074441 A1 | 4/2006 | Mcguckin, Jr. et al. |
| 2006/0149169 A1 | 7/2006 | Nunomura et al. |
| 2006/0161098 A1 * | 7/2006 | Nita ................ A61B 17/22004 604/22 |
| 2006/0206039 A1 | 9/2006 | Wilson et al. |
| 2006/0264809 A1 | 11/2006 | Hansmann et al. |
| 2007/0032749 A1 | 2/2007 | Overall et al. |
| 2007/0161945 A1 | 7/2007 | Nita et al. |
| 2007/0178768 A1 | 8/2007 | Harshman et al. |

(56) References Cited

U.S. PATENT DOCUMENTS

| | | |
|---|---|---|
| 2007/0181157 A1* | 8/2007 | Dadourian ............ B08B 9/0325 |
| | | 134/22.12 |
| 2008/0033284 A1 | 2/2008 | Hauck |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2008/0294037 A1 | 11/2008 | Richter |
| 2009/0017293 A1 | 1/2009 | Arai et al. |
| 2009/0143795 A1 | 6/2009 | Robertson |
| 2009/0264833 A1* | 10/2009 | Boyle, Jr. .............. A61B 90/70 |
| | | 604/257 |
| 2010/0004558 A1 | 1/2010 | Frankhouser et al. |
| 2010/0023037 A1 | 1/2010 | Nita et al. |
| 2010/0069854 A1 | 3/2010 | Okoh et al. |
| 2010/0076454 A1 | 3/2010 | Bos |
| 2010/0121144 A1 | 5/2010 | Farhadi |
| 2010/0217306 A1 | 8/2010 | Raabe et al. |
| 2010/0268206 A1 | 10/2010 | Manwaring et al. |
| 2011/0046522 A1 | 2/2011 | Chan et al. |
| 2011/0105960 A1 | 5/2011 | Wallace |
| 2011/0106019 A1* | 5/2011 | Bagwell ............... B08B 9/0436 |
| | | 604/267 |
| 2011/0130834 A1 | 6/2011 | Wilson et al. |
| 2011/0172642 A1* | 7/2011 | Lareau ............... A61M 25/0017 |
| | | 604/523 |
| 2011/0196399 A1 | 8/2011 | Robertson et al. |
| 2011/0196403 A1 | 8/2011 | Robertson et al. |
| 2011/0237982 A1 | 9/2011 | Wallace |
| 2011/0313328 A1 | 12/2011 | Nita |
| 2012/0010506 A1 | 1/2012 | Ullrich |
| 2012/0109021 A1 | 5/2012 | Hastings et al. |
| 2012/0130475 A1 | 5/2012 | Shaw |
| 2012/0217306 A1 | 8/2012 | Morrill Webb et al. |
| 2012/0238916 A1 | 9/2012 | Nita et al. |
| 2012/0238946 A1 | 9/2012 | Nita et al. |
| 2012/0311844 A1 | 12/2012 | Nita et al. |
| 2012/0330196 A1 | 12/2012 | Nita |
| 2013/0046297 A1 | 2/2013 | Lingeman et al. |
| 2013/0060169 A1 | 3/2013 | Yamada |
| 2013/0199019 A1* | 8/2013 | Garbini ................. A61B 6/485 |
| | | 29/729 |
| 2013/0237930 A1* | 9/2013 | Mulvihill ............ A61J 15/0026 |
| | | 604/264 |
| 2013/0331652 A1 | 12/2013 | Okamoto |
| 2013/0338580 A1 | 12/2013 | Yamatani et al. |
| 2014/0005706 A1 | 1/2014 | Gelfand et al. |
| 2014/0012087 A1 | 1/2014 | Omoto |
| 2014/0039491 A1 | 2/2014 | Bakos et al. |
| 2014/0171804 A1 | 6/2014 | Van Hoven |
| 2014/0236118 A1 | 8/2014 | Unser et al. |
| 2014/0243712 A1 | 8/2014 | Humayun et al. |
| 2014/0276369 A1* | 9/2014 | Banko ................ A61F 9/00745 |
| | | 604/22 |
| 2014/0336665 A1* | 11/2014 | Gavala ............. A61B 17/22012 |
| | | 606/128 |
| 2014/0350401 A1 | 11/2014 | Sinelnikov |
| 2014/0358028 A1 | 12/2014 | Vetter et al. |
| 2015/0025451 A1* | 1/2015 | Banko ................... A61M 1/774 |
| | | 604/35 |
| 2015/0025544 A1 | 1/2015 | Nita et al. |
| 2015/0073357 A1 | 3/2015 | Bagwell et al. |
| 2015/0105621 A1 | 4/2015 | Farhadi |
| 2015/0105715 A1 | 4/2015 | Pikus et al. |
| 2015/0133918 A1 | 5/2015 | Sachar |
| 2015/0148795 A1 | 5/2015 | Amos et al. |
| 2015/0157443 A1 | 6/2015 | Hauser et al. |
| 2015/0190660 A1 | 7/2015 | Sarge et al. |
| 2015/0231313 A1* | 8/2015 | O'Keefe ................. A61M 25/00 |
| | | 604/266 |
| 2015/0297258 A1 | 10/2015 | Escudero et al. |
| 2015/0359651 A1 | 12/2015 | Wübbeling |
| 2016/0038165 A1* | 2/2016 | Cook ................ A61B 17/22012 |
| | | 606/128 |
| 2016/0128717 A1 | 5/2016 | Nita |
| 2016/0135835 A1 | 5/2016 | Onuma |
| 2016/0183956 A1 | 6/2016 | Nita |
| 2016/0271362 A1 | 9/2016 | Van Liere |
| 2016/0287223 A1* | 10/2016 | Hingston .................. A61B 8/12 |
| 2016/0328998 A1 | 11/2016 | Nita et al. |
| 2016/0331645 A1* | 11/2016 | Bagwell ........... A61B 17/22012 |
| 2016/0338722 A1 | 11/2016 | Nita et al. |
| 2016/0361528 A1* | 12/2016 | Kanz ...................... A61N 7/022 |
| 2016/0367284 A1 | 12/2016 | Nita et al. |
| 2017/0065288 A1 | 3/2017 | Imai et al. |
| 2017/0128090 A1 | 5/2017 | Sarge |
| 2017/0265886 A1 | 9/2017 | Nita et al. |
| 2017/0354428 A1 | 12/2017 | Nita et al. |
| 2018/0042636 A1 | 2/2018 | Nita |
| 2018/0140321 A1 | 5/2018 | Deepa |
| 2018/0168668 A1 | 6/2018 | Zheng |
| 2018/0177515 A1 | 6/2018 | Boyle et al. |
| 2018/0197856 A1 | 7/2018 | Chou et al. |
| 2018/0221040 A1 | 8/2018 | Roll Hoye |
| 2018/0280005 A1 | 10/2018 | Parmentier |
| 2018/0280044 A1 | 10/2018 | Nita et al. |
| 2019/0059920 A1* | 2/2019 | Nita ................. A61B 17/22012 |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| DE | 10146011 A1 | 4/2003 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |

(56) References Cited

FOREIGN PATENT DOCUMENTS

| WO | 9925412 | A2 | 5/1999 |
|---|---|---|---|
| WO | 0053341 | A1 | 9/2000 |
| WO | 0067830 | A1 | 11/2000 |
| WO | 02094103 | A1 | 11/2002 |
| WO | 03039381 | A1 | 5/2003 |
| WO | 2004012609 | A1 | 2/2004 |
| WO | 2004093736 | A2 | 11/2004 |
| WO | 2004112888 | A2 | 12/2004 |
| WO | 2005053769 | A2 | 6/2005 |
| WO | 2005112770 | A1 | 12/2005 |
| WO | 2006049593 | A1 | 5/2006 |
| WO | 2013109269 | A1 | 7/2013 |
| WO | 2014022716 | A2 | 2/2014 |
| WO | 2014105754 | A1 | 7/2014 |
| WO | 2014106847 | A1 | 7/2014 |
| WO | 2018097856 | A1 | 5/2018 |
| WO | 20180187159 | A1 | 10/2018 |

OTHER PUBLICATIONS

Definition of the term "coupled", retrieved on May 18, 2013 <http://www.merriam-webster.com/dictionary/couple> 1 page total.

"E-Beam Theory" RDI-IBA Technology Group, downloaded from web on Oct. 8, 2002 <http://www.e-beamrdi/EbeamTheory.htm> 2 pages total.

Office Action dated May 20, 2010 from Japanese Application No. 2006-541200 filed on Oct. 25, 2004.

Office Action dated Oct. 11, 2012 from Japanese Application No. 2010-181956.

Extended European Search Report dated Mar. 5, 2012 for European Application No. 12153606.4-1269.

Margaret Fyfe et al., Mast cell degranulation and increased vascular permeability induced by therapeutic' ultrasound in the rate ankle joint, Br. J. exp. Path., 1984, vol. 65, pp. 671-676.

"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.

Paul Yock et al., Catheter-Based Ultrasound Thrombolysis Shake, Rattle, and Repertuse, https://doi.org/10.1161/01.CIR.95.6.1360 Circulation. 1997;95:1360-1362 Originally published Mar. 18, 1997.

Noone, D.: Experimental and Numerical Investigation of Wire Waveguides for Therapeutic Ultrasound Angioplasty. M.Eng. Dublin City University. 2008.

Definition of the term "connected", retrieved on Sep. 21, 2013. <www.thefreedictionary.com/connected> 1 page total.

Supplemental European Search Report dated Nov. 5, 2009 for European Application No. EP03766931.

International Search Report dated Oct. 28, 2003 for PCT Application No. PCT/US2003/023468.

Extended European Search Report dated Mar. 22, 2012 for European Application No. EP11188799.

International Search Report dated Dec. 23, 2005 for PCT Application No. PCT/US2004/019378.

Extended European Search Report for Patent Application No. 06718204.8, dated May 30, 2012.

International Search Report dated Aug. 1, 2013 for PCT Application No. PCT/US2013/053306.

International Preliminary Report dated Aug. 1, 2013 for PCT Application No. PCT/US2013/053306.

Written Opinion dated Aug. 1, 2013 for PCT Application No. PCT/US2013/053306.

Supplemental European Search Report dated Apr. 29, 2009 for European Application No. EP 04711207.3.

Office Action dated Aug. 3, 2010 from Japanese Application No. 2006-517355 filed on Jun. 16, 2004.

Office Action dated Jan. 26, 2010 from Japanese Application No. 2006-517355 filed on Jun. 16, 2004.

International Preliminary Report and Written Opinion dated Aug. 1, 2017 for PCT Application No. PCT/US2017/030675.

International Preliminary Report and Written Opinion dated Feb. 6, 2018 for PCT Application No. PCT/US2018/017022.

Japanese Office Action for Japanese Application No. 2010-134566, dated Mar. 2, 2012.

Sehgal, et al., Ultrasound-Assisted Thrombolysis, Investigative Radiology, 1993, vol. 28, Issue 10, pp. 939-943.

Siegel, et al., "In Vivo Ultrasound Arterial Recanalization of Atherosclerotic Total Occlusions", Journal of the American College of Cardiology, Feb. 1990, vol. 15, No. 2, pp. 345-351.

"What is Electron Beam Curing?" downloaded from web on Nov. 14, 2002, 4 pages total. <http://www.ms.oml.gov/researchgroups/composites/new%20orccmt%20pages/pages/ebwha>.

EP Extended Search Report dated Aug. 13, 2009; Application 04710537.5-1269, 5 pages.

* cited by examiner

ULTRASOUND DEVICES FOR REMOVING CLOTS FROM CATHETERS AND RELATED METHODS

This application claims the benefit of U.S. Provisional Patent Application Ser. No. 62/435,723, the disclosure of which is incorporated herein by reference.

TECHNICAL FIELD

This document relates generally to the catheter art and, more particularly, to ultrasound devices for removing obstructions, such as clots, from catheters and related methods.

BACKGROUND

Various therapies involve the installation of certain types of catheters for prolonged use. Examples include "PICC" catheters (peripherally inserted central catheters) for installation in the peripheral vascular space, hemodialysis catheters (sometimes simply referred to as "dialysis" catheters), and implantable ports associated with catheters. In view of the extended use of these devices for circulating blood to or from a patient undergoing a particular therapy, clots may form that impede flow, which can lead to complications. Manual cleaning of the catheters is possible, but challenging, and may also deleteriously require removing the device from the patient, which can be a complicated process.

Accordingly, a need is identified for devices and related methods for removing obstructions, such as clots, from specific types of indwelling catheters. The devices and method should be easy and inexpensive to implement on a variety of indwelling catheters, and would be able to remove any obstructions without considerable effort to allow the therapy to continue unabated.

SUMMARY

According to a first aspect of the disclosure, an apparatus for use in a medical procedure involving a vascular space. The apparatus comprises a catheter having a lumen adapted for communicating fluid between a distal end for insertion in the vascular space and a proximal end. A transducer is adapted for removably connecting to the catheter for contacting the fluid and transmitting energy through the fluid in the lumen for dissolving an obstruction therein. A suction is also provided for removing any debris from the obstruction in the lumen of the catheter.

In one embodiment, the catheter comprises at least one port for receiving the transducer or the suction. The transducer may comprise a head for positioning in the port for contacting a fluid in the lumen of the catheter. The transducer may further comprise a wave guide, such as for example a wire, for passing into the port, which wave guide may be a single use component. The wave guide may be removably connected to the transducer, and may also be substantially similar in length to a length of the lumen.

The transducer may be connected directly to the catheter. The transducer may further comprise a passage, and the suction may be adapted for removing any debris in the lumen through the passage of the transducer. The catheter may comprise a first port for associating with the transducer and a second port for associating with the suction. A housing of the transducer may form a portable, handheld unit, and may comprise a self-contained power source, such as a battery. The housing may include an ultrasound generator.

The catheter may take a variety of forms. The catheter may comprise a peripherally inserted central line catheter (PICC). The catheter may comprise a hemodialysis catheter. The catheter may also comprise an implantable port.

A further aspect of the disclosure pertains to an apparatus for use during a medical procedure involving a vascular space. The apparatus includes a catheter having a tubular body including a lumen adapted for communicating fluid between a distal end for insertion in the vascular space and a proximal end. A transducer is adapted for removably connecting to the tubular body of the catheter for transmitting energy through the lumen for dissolving an obstruction therein.

The transducer may include a tubular wave guide adapted for removably connecting to the catheter for contacting the fluid and transmitting energy through the fluid in the lumen for dissolving an obstruction therein. The lumen may have a length between the proximal and the distal end, and the transducer includes a wave guide having a length corresponding to the lumen length.

Still a further aspect of the disclosure pertains to a catheter including an embedded ultrasonic transducer. The ultrasonic transducer may be embedded in a connector, a hub, a tube, or any combination thereof.

Yet another aspect of the disclosure pertains to an implantable port including an embedded ultrasonic transducer.

BRIEF DESCRIPTION OF THE DRAWING FIGURES

The above and further advantages of the present invention may be better understood by referring to the following description in conjunction with the accompanying drawings in which.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Figure 1:
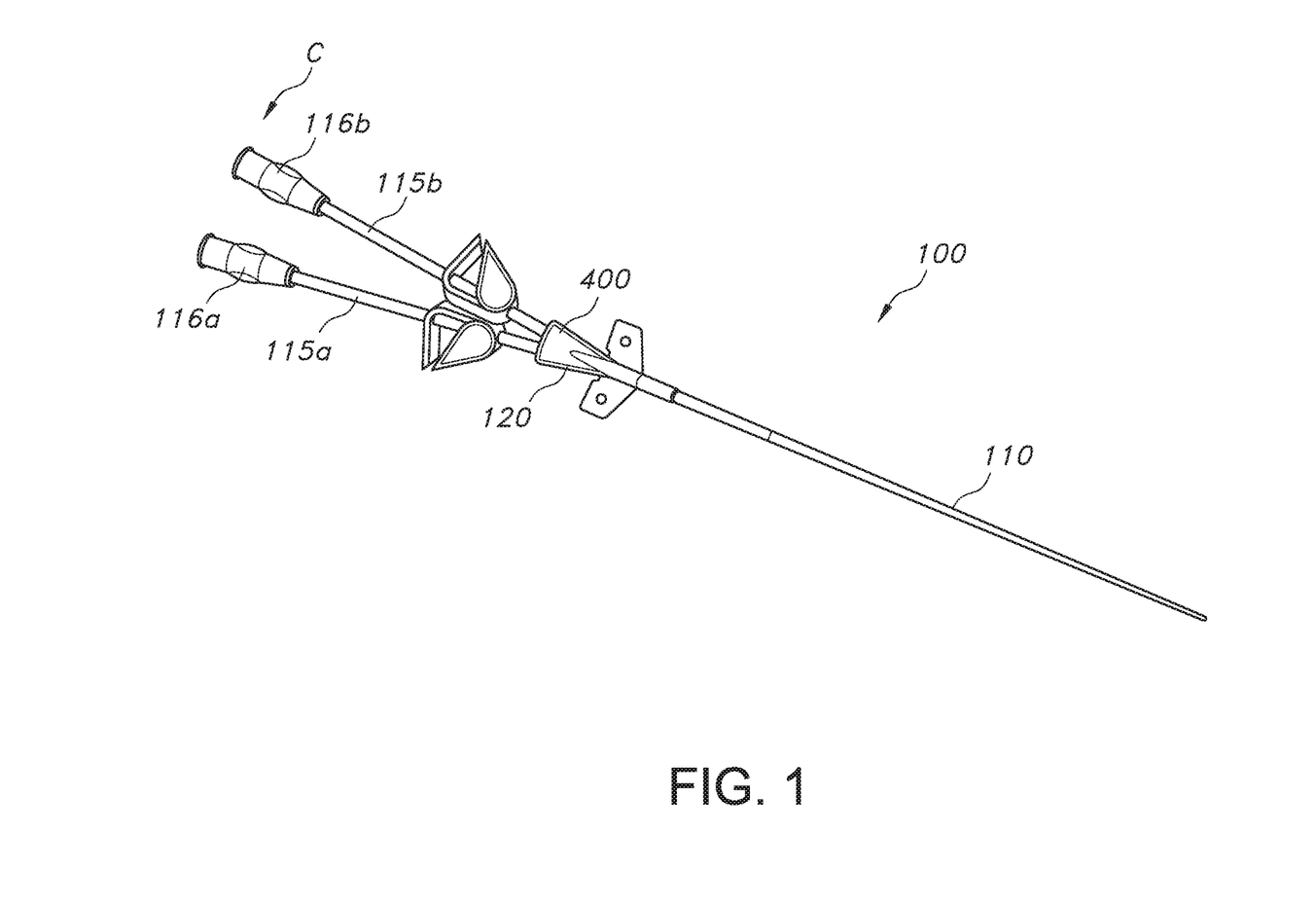
FIG. 1 is a perspective view of a catheter.

Referring to FIG. 1, a peripherally inserted central line catheter (PICC) 100 is shown. The PICC 100 may be constructed from a catheter 110, such as an extruded polymer tube with one or more lumens. The catheter 110 may be affixed to corresponding extension leg tubing 115a, 115b via a junction hub 120. The extension leg tubing 115a, 115b may be affixed to connectors C, such as luer hubs 116a, 116b, designed to connect each of the extension legs 115a, 115b to a medical device, such as a syringe or further tubing for communicating fluid or other substances to or from the catheter 110.

Figure 2:
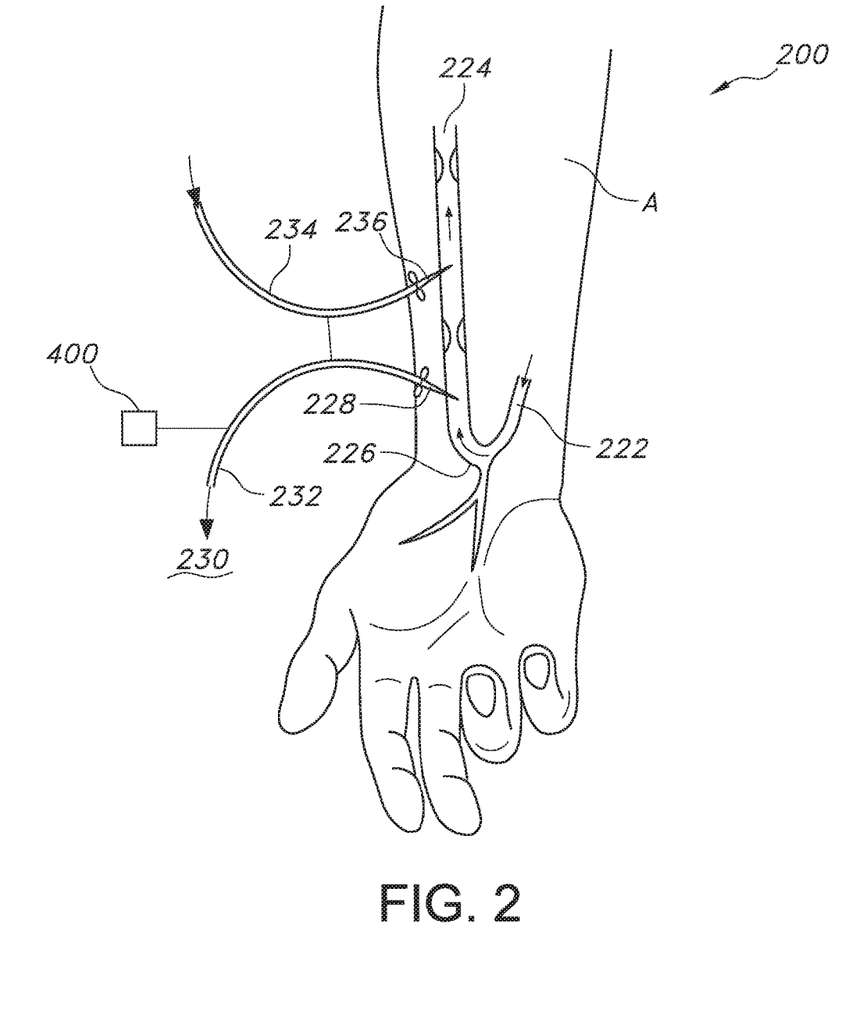
FIG. 2 is a schematic view of an arrangement for performing hemodialysis.

FIG. 2 illustrates a hemodialysis catheter 200. In this example, there is shown the human forearm A and, diagrammatically, beneath the skin, an arterial lumen 222, a venous lumen 224 and, between them, an arteriovenous fistula 226. A first tube 232 connects to a dialysis needle 228, which taps blood for a dialysis machine 230, and a return flow tube 234 from the machine delivers blood back to the patient via a second dialysis needle 236. The tubes 232, 234 may each include a connector (not shown).

Figure 3:
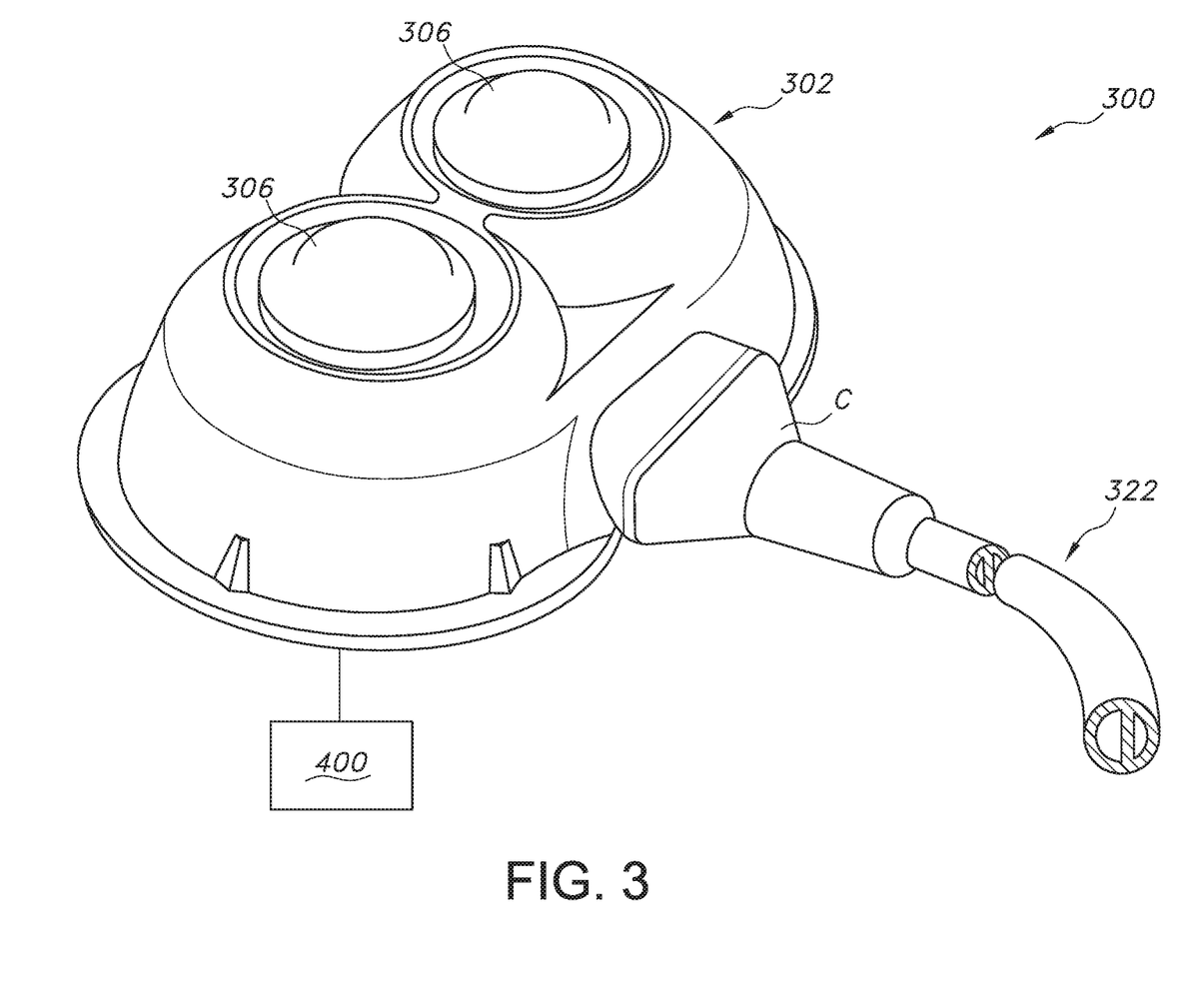
FIG. 3 is a perspective view of a port.

A third type of device illustrated in FIG. 3 is a catheter 300 connected to an implantable port 302. The port 302 may comprise chambers enclosed by a septum 306 which defines the top of each chamber. This assembly is then attached to the catheter 300, which may for example include an elongated dual lumen tube 322 having a connector C at one end, which as illustrated may have a different shape. The port 302 and tube 322 may be implanted in a patient for receiving substances, such as medicines or nutrients, from external to the vasculature.

As noted above, any of these catheters 100, 200, 300 in use may be blocked by the formation of a partial or full obstruction, such as a blood clot. In a first embodiment, and with reference to FIG. 4, an ultrasound transducer 400 (shown schematically only) is proposed for removing any obstruction by delivering ultrasonic energy to a fluid F in the lumen of the catheter 100, 200, 300. The fluid F may comprise saline, which may be introduced through a first port $P_1$ formed in the connector C for connecting any of the catheters 100, 200, 300 to an external device (e.g., port, dialysis machine, syringe, etc.).

Figure 4:
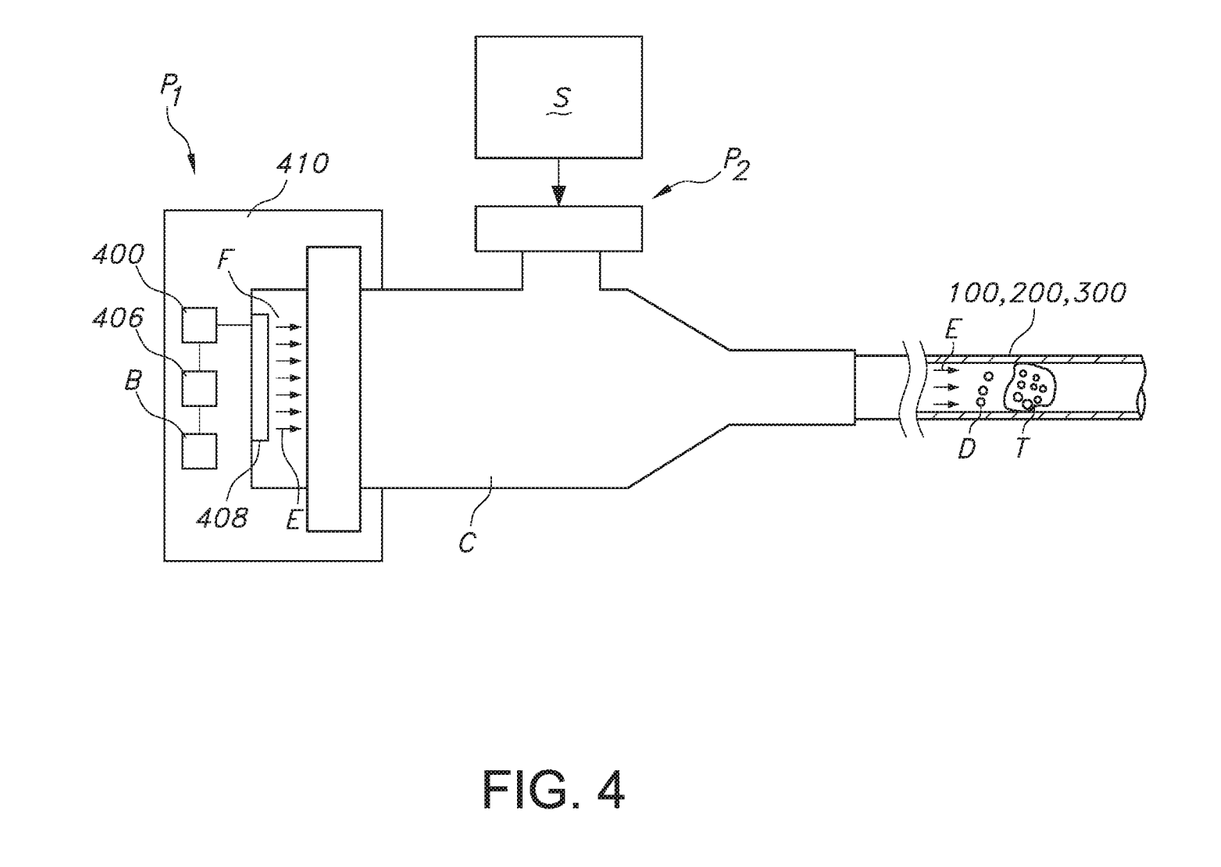
FIG. 4 is a partially cross-sectional, partially cutaway view of a catheter including an ultrasonic generator.

The transducer 400 as shown may include a horn 408 for contacting and transmitting vibrational energy E to the fluid F from an associated generator 406. The transducer 400 may be associated with a transducer housing 410 adapted to couple in a sealed, but removable fashion to the proximal end of the connector C (such as by at least partially receiving it in a chamber formed in the housing 410 and including the horn). Using the fluid F as a conduit, this remotely transmitted energy may serve to break up a clot or thrombus T in the lumen of the catheter 100, 200, 300 in an efficient manner and without the need for complicated techniques or the use of thrombolytic agents (which would remain optional to facilitate clearing the clot or thrombus).

Figure 5:
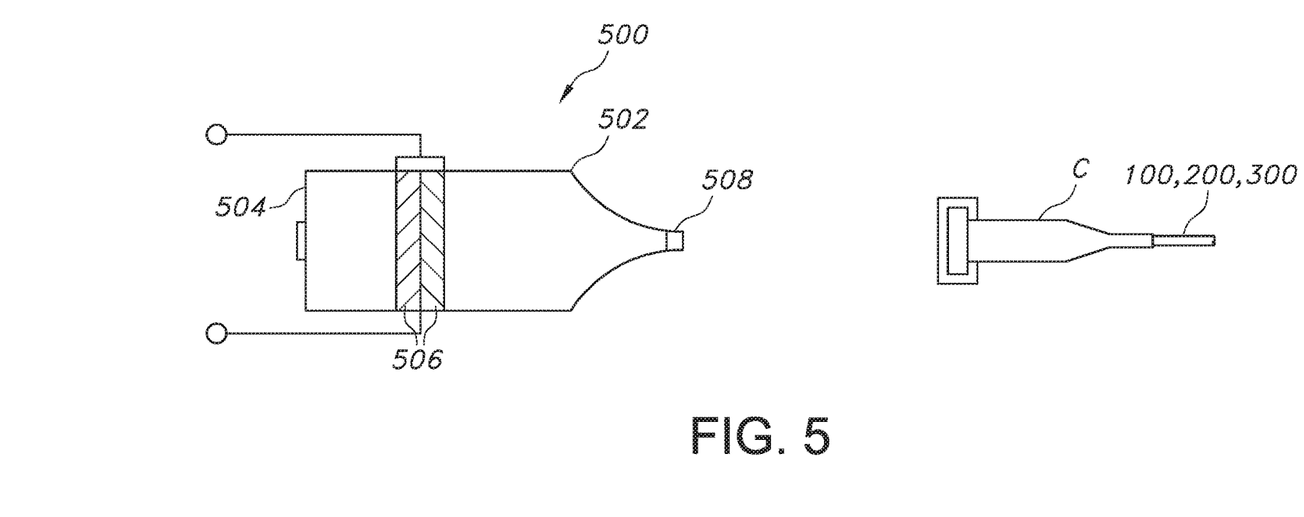
FIGS. 5 and 5A are partially assembled and exploded views of one catheter assembly according to the disclosure.
Figure 5A:
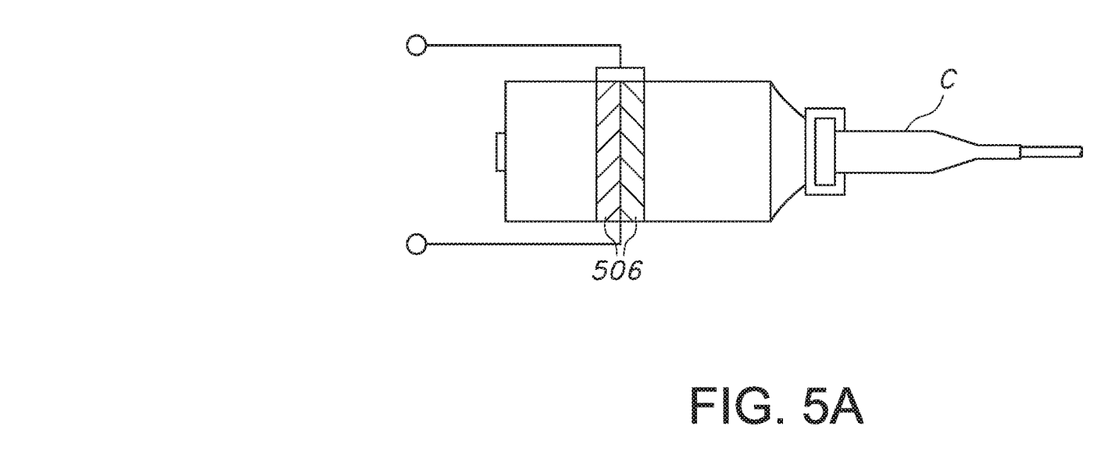

FIGS. 5 and 5A illustrate a different embodiment of a transducer 500, which comprises a front mass 502, a back mass 504, and a piezoelectric generator 506 between the two structures and connected by wires to a source of power. A horn 508 is provided at the narrowed end of the transducer 500 for insertion into the open end of the connector C to transmit vibratory energy thereto, such as in contact with a fluid therein.

Figure 6:
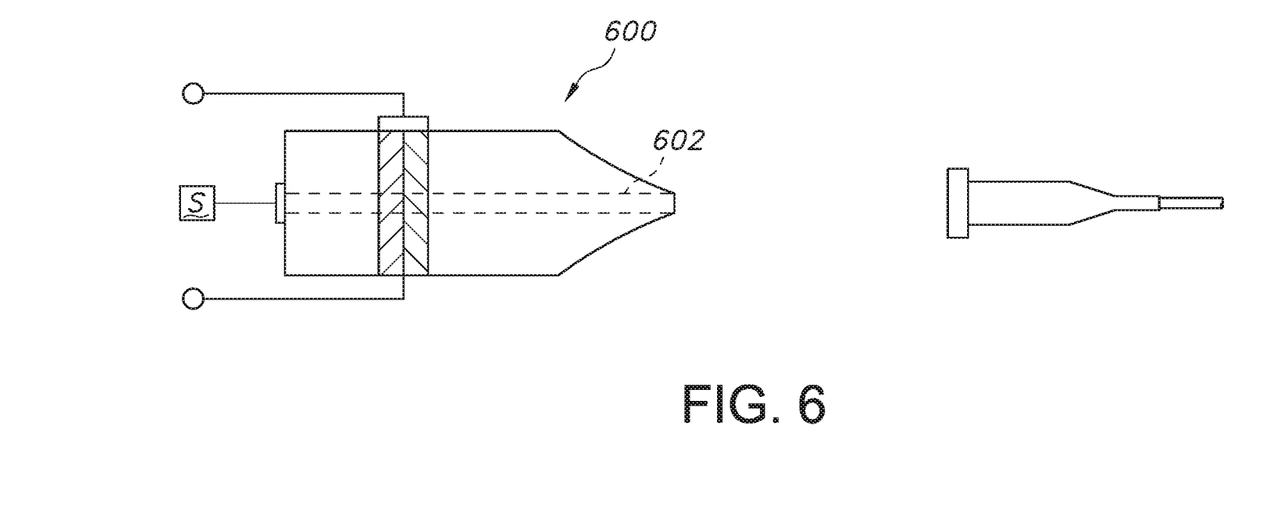
FIGS. 6 and 6A are partially assembled and exploded views of another catheter assembly according to the disclosure.
Figure 6A:
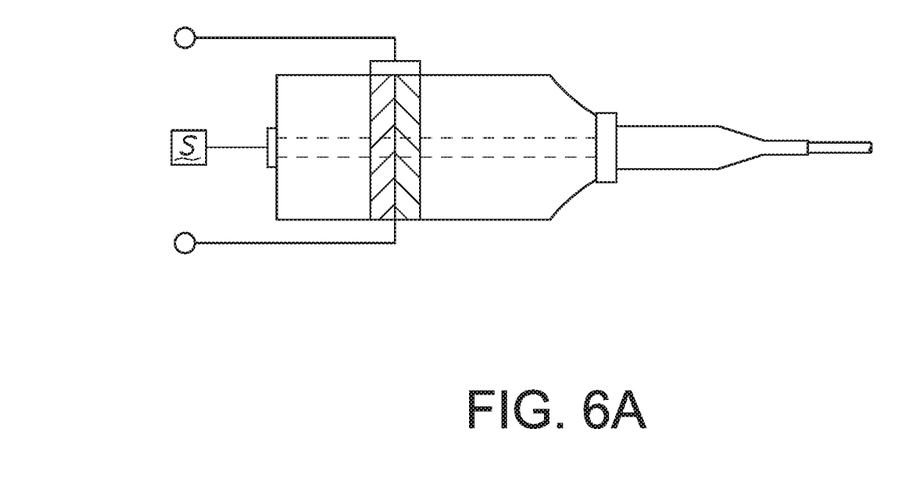

During or after the application of ultrasonic energy, a suction S (i.e., a force that causes a fluid or solid to be drawn into an interior space or to adhere to a surface because of the difference between the external and internal pressures) may be applied to remove any dislodged debris D from the obstruction (such as clot or thrombus T) using a vacuum (such as by a syringe or like device). As indicated in FIG. 4, this may be done using a second port $P_2$ in the connector C, which may include a removable cap (not shown) when not in use to create a sealed system. Alternatively, as shown in FIG. 6, the transducer 600 itself may include a passage 602 to which a suction S may be applied. This may be done while the transducer remains mounted to the connector, as indicated in FIG. 6A, which thus allows for concurrent vibration and suction to be applied. Still another option is to remove the transducer 400, 500 without a passage from the mounted condition, and apply suction directly to the connector C. As can be appreciated, the process may be repeated as necessary or desired without disrupting the connection between the catheter 100, 200, 300 and the associated patient.

Figure 7:
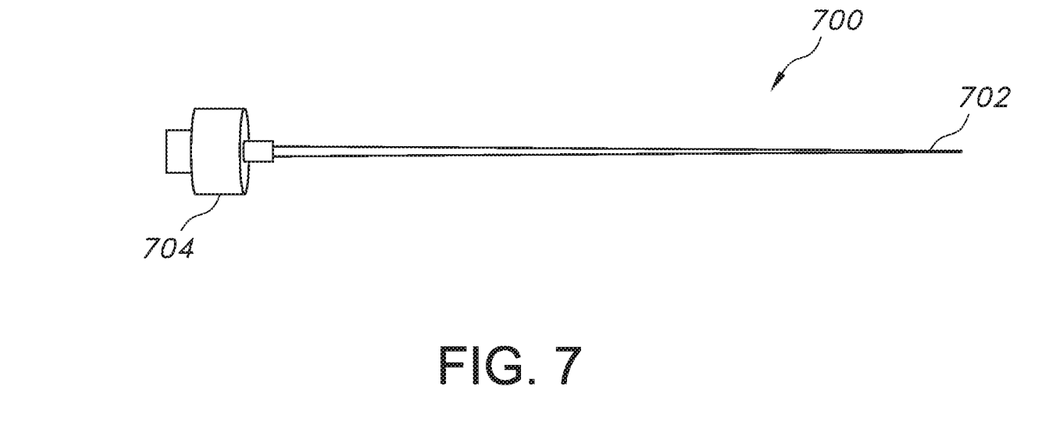
FIGS. 7 and 7A are photographs illustrating a core wire.

In a further embodiment, and with reference to FIG. 7, delivering ultrasonic energy to the catheter 100, 200, 300 and, in particular, a lumen may be achieved by inserting an elongated wave guide 700 into the lumen and applying energy thereto, such as from the generator 506 of transducer 500. The wave guide 700 may comprise a thin wire having a diameter slightly less than an inner diameter of the catheter lumen, and a length matching the length of the lumen. This ensures that the energy may be delivered to even the distal end thereof when fully inserted. Once the obstruction is cleared or substantially cleared, suction may be applied to the catheter 100, 200, 300, such as by one of the ports $P_1$, $P_2$ of connector C (including possibly via a passage 602 in the transducer 600), to remove any dislodged debris D.

The wave guide 700 may also comprise a removable wire or tube for being inserted into a socket in the transducer 400, 500, 600. This allows for the wave guide 700 to be a single use component, and avoids the need for re-sterilization. The transducer 400, 500, 600 may be a single use component as well, but may also be cleaned and reused with a different wave guide 700 for a subsequent procedure. In the case of a tube, the wave guide 700 may be used both for providing ultrasound energy and suction to the lumen of the catheter 100, 200, 300 including the obstruction. In the FIG. 6 embodiment, the suction S may be applied directly to a tubular waveguide (not shown) such as via passage 602.

Figure 7A:
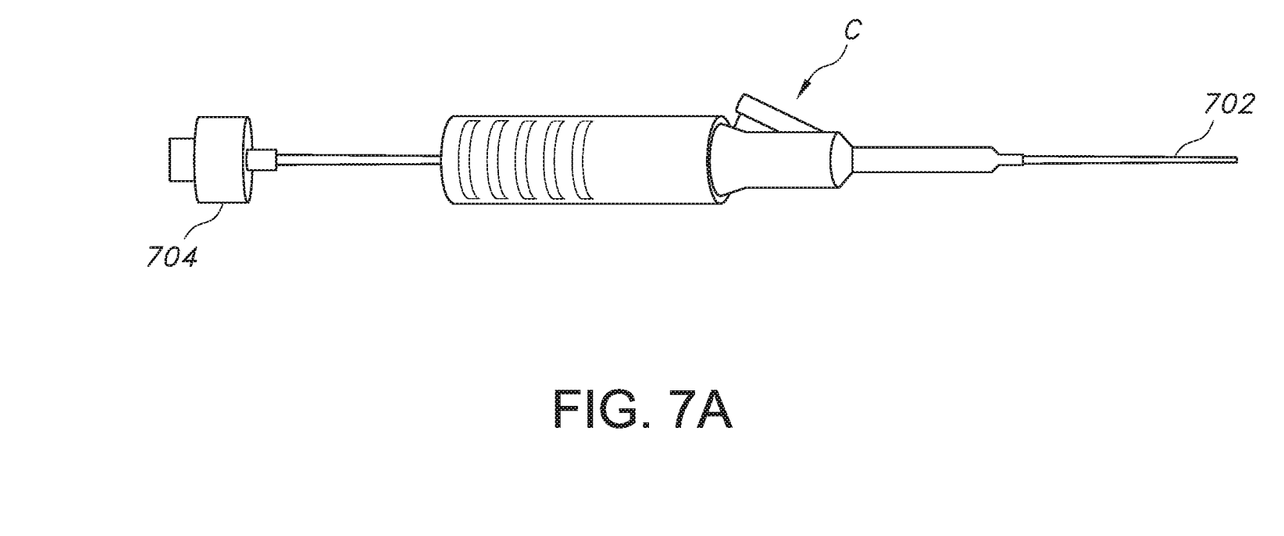

As shown in FIGS. 7 and 7A, the wave guide 700 may comprise a core wire 702 having a first end adapted for connecting to the transducer 400, 500, 600. The core wire 702 (which may comprise Nitinol) may be connected to a connector 704, such as by crimping. The connector 704 may be threaded, and may then be screwed into the transducer horn 408, 508 to provide a solid mechanical connection so that ultrasonic energy can be transmitted. FIG. 7A includes an example of connector C, but lacks any catheter tube.

Figure 8:
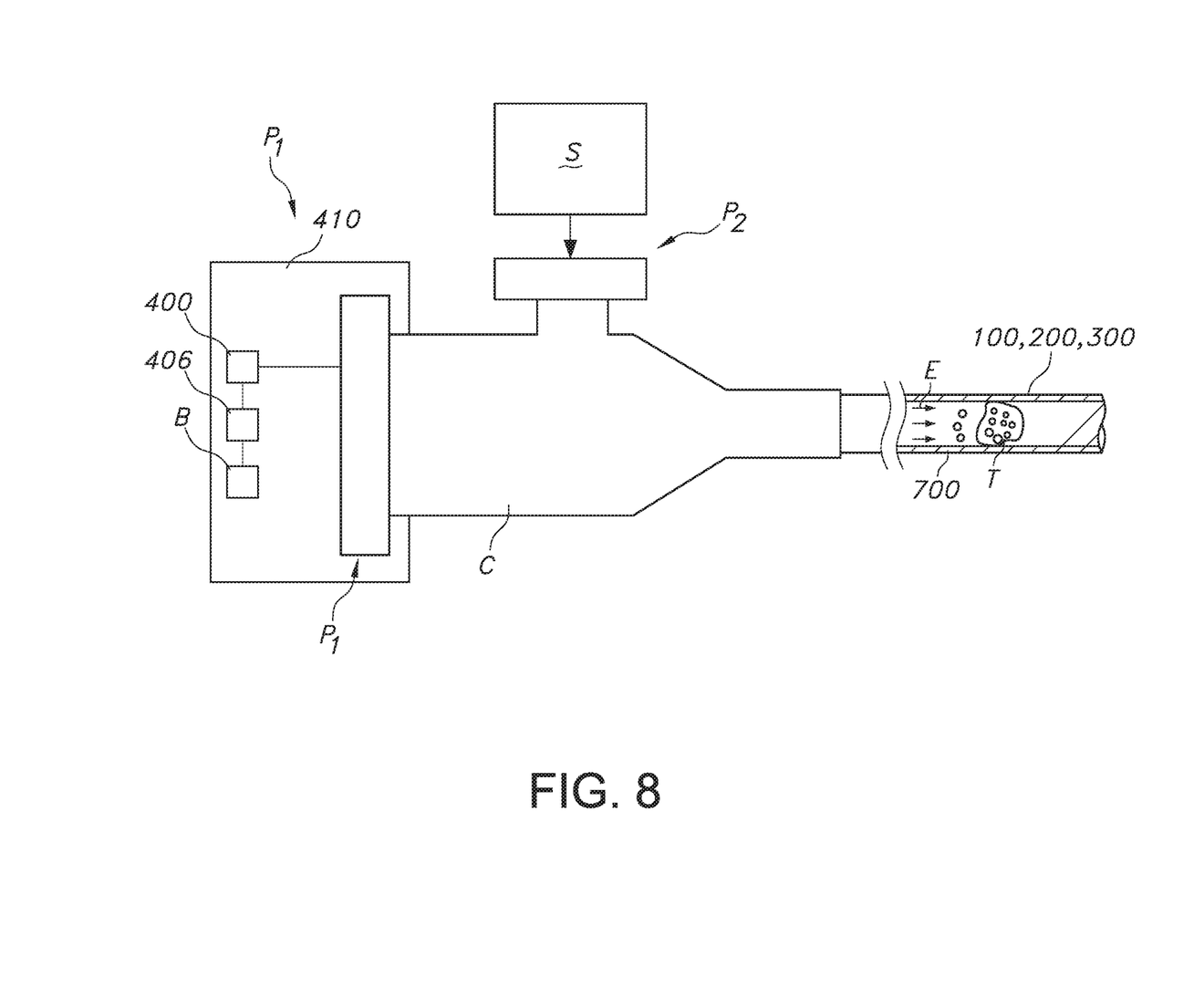
FIG. 8 is a partially cross-sectional, partially cutaway view of a still another catheter including an ultrasonic generator.

In a further embodiment, as indicated in FIG. 8, the transducer 400 is adapted for delivering ultrasonic energy to the catheter 100, 200, 300 itself, such as by forming a direct connection between the two structures. When the transducer 400 is coupled to the catheter 100, 200, 300, such as adjacent to the first port $P_1$ and energized, the vibrational energy is thus transmitted to the catheter body (which is tubular, and thus functions as a wave guide 700) and serves to break up any obstruction in the lumen, such as clot. Suction S may then be applied as previously described, including through one of the ports $P_1$, $P_2$ of connector C (including possibly via passage 602 in the transducer 600) to remove any dislodged material.

In yet another embodiment, the transducer 400 is embedded in the catheter 100, 200, 300. Thus, as indicated in FIG. 1, the transducer 400 may be embedded in a hub 120, or alternatively in one or both of the connectors C. As indicated in FIG. 2, the transducer 400 may also be embedded in a body of the tube forming part of catheter 200. FIG. 4 illustrates that the transducer 400 may also be embedded in the port.

Referring back to FIG. 4, the transducer 400 may include a self-contained power source, such as a battery B (which may be removable or rechargeable) for powering the associated generator 406. These components may be contained in a single housing 410 of transducer 400. This allows for a compact, portable transducer 400 to be constructed, which can be held in a pocket or the like for ready use with a variety of catheters or applications.

The transducer 400 may comprise a Langevin type transducer or a piezoelectric ceramic type of transducer. The ultrasound frequency may be in the range of 10 kHz to 1 MHz. The optimal energy used may vary depending on the particular catheter or the nature of the obstruction.

Each of the following terms written in singular grammatical form: "a", "an", and "the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated components), feature(s), characteristic"), parameters), integers), or step(s), and does not preclude addition of one or more additional components), feature(s), characteristics), parameters), integer(s), step(s), or groups thereof. Each of these terms is considered equivalent in meaning to the phrase "consisting essentially of. Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

What is claimed:

1. A system for use in a therapeutic procedure involving a vascular space, comprising:
    an indwelling catheter configured to facilitate the therapeutic procedure having a proximal end, a distal end adapted for insertion in the vascular space, and a lumen adapted for communicating a fluid between the distal end and the proximal end; and
    a cleaning apparatus configured to clear an obstruction within the indwelling catheter during the therapeutic procedure, the cleaning apparatus comprising:
        a transducer adapted for removably connecting to the indwelling catheter, the transducer configured to contact the fluid and transmit ultrasound energy in a distal direction via the fluid in the lumen at a frequency sufficient for dissolving the obstruction therein with the fluid, the transducer having a passage extending therethrough; and
        a suction generator removably coupled to the transducer, the suction generator configured for fluid communication with the lumen via the passage through the transducer, the suction generator configured to generate a negative pressure in the lumen of the indwelling catheter,
    wherein the cleaning apparatus is configured to use the negative pressure to remove any debris from the obstruction in the lumen of the indwelling catheter, the cleaning apparatus is configured to operate the transducer and the suction generator concurrently during the therapeutic procedure without disrupting a connection between the indwelling catheter and the vascular space.

2. The system of claim 1, wherein the indwelling catheter comprises at the proximal end a first port for receiving the transducer.

3. The system of claim 2, wherein the transducer comprises a wave guide for passing into the first port.

4. The system of claim 3, wherein the wave guide comprises a tube.

5. The system of claim 3, wherein the wave guide is a single use component.

6. The system of claim 3, wherein the wave guide is removably connected to the transducer.

7. The system of claim 3, wherein a length of the wave guide is substantially similar to a length of the lumen.

8. The system of claim 2, wherein the transducer comprises a head for positioning in the first port for contacting the fluid in the lumen of the indwelling catheter.

9. The system of claim 1, wherein the transducer is connected directly to the indwelling catheter.

10. The system of claim 1, wherein the indwelling catheter comprises a first port for associating with the transducer and a second port for communicating the fluid to the indwelling catheter.

11. The system of claim 1, wherein the transducer comprises a housing forming a portable, handheld unit.

12. The system of claim 11, wherein the housing includes a power source.

13. The system of claim 11, wherein the housing includes an ultrasound generator.

14. The system of claim 1, wherein the indwelling catheter comprises a PICC.

15. The system of claim 1, wherein the indwelling catheter comprises a hemodialysis catheter.

16. The system of claim 1, wherein the indwelling catheter comprises an implantable port.

17. An apparatus for use in clearing an obstruction in a lumen of a catheter during a therapeutic procedure involving a vascular space, the catheter having a proximal end, a distal end adapted for insertion in the vascular space, and the lumen adapted for communicating a fluid between the distal end and the proximal end, the apparatus comprising:
   a transducer adapted for removably connecting to the catheter, the transducer configured to contact the fluid and transmit ultrasound energy in a distal direction via the fluid in the lumen at a frequency sufficient for dissolving an obstruction therein with the fluid, the transducer having a passage extending therethrough; and
   a suction generator removably coupled to the transducer, the suction generator configured for fluid communication with the lumen via the passage through the transducer, the suction generator configured to generate a negative pressure in the lumen of the catheter,
   wherein the suction generator and transducer are proximal of the distal end of the catheter, the apparatus is configured to use the negative pressure to remove any debris from the obstruction in the lumen of the catheter while the distal end of the catheter remains in the vascular space, the cleaning apparatus is configured to operate the transducer and the suction generator concurrently during the therapeutic procedure.

* * * * *

UNITED STATES PATENT AND TRADEMARK OFFICE
CERTIFICATE OF CORRECTION

PATENT NO. : 11,596,726 B2
APPLICATION NO. : 15/845187
DATED : March 7, 2023
INVENTOR(S) : Zheng Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 729 days.

Signed and Sealed this
Thirty-first Day of December, 2024

Derrick Brent
*Acting Director of the United States Patent and Trademark Office*